United States Patent [19]
Phillips

[11] Patent Number: 5,685,879
[45] Date of Patent: Nov. 11, 1997

[54] SURGICAL BONE WAX APPLICATOR

[76] Inventor: Arnold G. Phillips, 1420 Madison Dr., Buffalo Grove, Ill. 60089

[21] Appl. No.: 667,092

[22] Filed: Jun. 20, 1996

[51] Int. Cl.⁶ .................................................. A61B 17/56
[52] U.S. Cl. ........................... 606/86; 606/309; 424/426
[58] Field of Search ........................... 606/86, 92, 93; 604/289, 310, 309; 15/210.1, 235.4

[56]  References Cited

U.S. PATENT DOCUMENTS

| | | |
|---|---|---|
| 737,066 | 8/1903 | Bonar . |
| 932,388 | 8/1909 | Hartsock . |
| 1,852,114 | 4/1932 | Green . |
| 2,057,500 | 10/1936 | O'Connor . |
| 3,396,419 | 8/1968 | Richter et al. . |
| 3,591,299 | 7/1971 | Pharris ................................. 401/118 |
| 4,148,318 | 4/1979 | Meyer .................................... 604/3 |
| 4,308,633 | 1/1982 | Huffel et al. . |
| 5,383,879 | 1/1995 | Phillips . |

FOREIGN PATENT DOCUMENTS

| | | |
|---|---|---|
| 1265013 | 1/1990 | Canada . |
| 2834801 | 2/1980 | Germany . |

*Primary Examiner*—Michael Buiz
*Assistant Examiner*—David O. Reip
*Attorney, Agent, or Firm*—Welsh & Katz, Ltd.

[57]  ABSTRACT

A bone wax applicator having a foot plate and a handle, wherein the bone wax is secured to the lower surface of the foot plate and applied by holding the handle. The handle extends from the upper surface of the footplate near the center of the upper surface. A pattern is provided on the lower surface of the foot plate to better hold the bone wax. The lower surface is provided with a raised edge to better hold the wax. The wax itself may have a pattern or embossed or printed surface to provide more wax at the point of application and also to provide greater gripping power. Further, gripping structures are provided on the handle to prevent accidental slippage during use. The bone wax applicator includes radio-opaque material so that it can be readily identified from an x-ray image.

17 Claims, 2 Drawing Sheets

SURGICAL BONE WAX APPLICATOR

This invention relates to an instrument used during human and veterinary surgery and, more specifically, to an instrument utilized to stop bleeding from bone tissue during surgery involving cutting of bone tissue, such as in orthopedic, cardiothoracic, and neurological surgery.

BACKGROUND OF THE INVENTION

In various medical, veterinary, and dental surgical procedures, bone tissue must be cut to perform the required surgical procedure. Since bone tissue is living tissue, it will bleed when cut, resulting in loss of the patient's blood, which can present a serious and dangerous problem if not addressed in a timely and appropriate manner.

A composition known as bone wax has been implemented to retard bone tissue bleeding by applying the bone wax onto the bleeding area. While the use of bone wax is well known, no effective and convenient device for applying the wax has been developed.

Generally, surgical bone wax is available for purchase in sealed and sterile packages which are usually opened immediately before its application on the bleeding bone tissue. The packages can be difficult to open, especially when gloves are worn, for example, by doctors or nurses or surgery assistants.

In addition to the above-mentioned problems with current methods and devices for applying bone wax, because current methods and devices utilize the user's fingers in close proximity to the actually application of the wax, the user's view can be generally obstructed while the wax is being applied, thereby rendering an accurate application of the bone wax very difficult. Currently known methods and devices thus require the user's hand to be near the bleeding bone. The severed area of the bone which bleeds generally has jagged edges and spicules which can penetrate surgical gloves worn by the surgeon, and this is clearly not desirable.

SUMMARY OF THE INVENTION

Accordingly, an object of the present invention is to provide a better tool for accurately and efficiently applying bone wax, especially during surgery.

A further object of the present invention is to provide a tool which does not materially obstruct the user's view while applying the bone wax.

Another object of the present invention is to provide a tool which allows the user to keep his fingers further away from the jagged bone area, thus reducing the possibility of contamination to the user and/or the operative site.

Yet another object of the present invention is to provide a disposable tool for applying bone wax which is also radio-opaque so that the tool can be identified by an x-ray image if it is inadvertently left in the patient's body.

Another object of the present invention is to create a greater efficiency of the bone wax by physical methods such as patterning or embossing or printing.

In accordance with the present invention, all of these objects, as well as others not herein specifically identified, are achieved by the present invention of a bone wax applicator generally having a handle and a foot plate to which the bone wax is secured. The handle is provided with grips which reduce the possibility of slippage during use. The foot plate is generally planar and has an upper and lower surface. The foot plate is further defined by a front, two sides and a back. The upper surface has a center, near which the handle is attached. The lower surface can be provided with a raised edge along the sides and back of the foot plate. The foot plate can also be provided with a pattern to better hold the bone wax to the lower surface. The bone wax can also be provided with a pattern thus increasing surface area with respect to volume, thereby providing more bone wax at the point of application. Furthermore, patterned bone wax will also provide the user with greater gripping power of the wax as it is applied to the bleeding bone tissue.

BRIEF DESCRIPTION OF THE DRAWINGS

Further objects of the invention, taken together with additional features contributing thereto and advantages occurring therefrom, will be apparent from the following description of the invention when read in conjunction with the accompanying drawings, wherein.

DETAILED DESCRIPTION OF THE PREFERRED EMBODIMENTS

Figure 1:
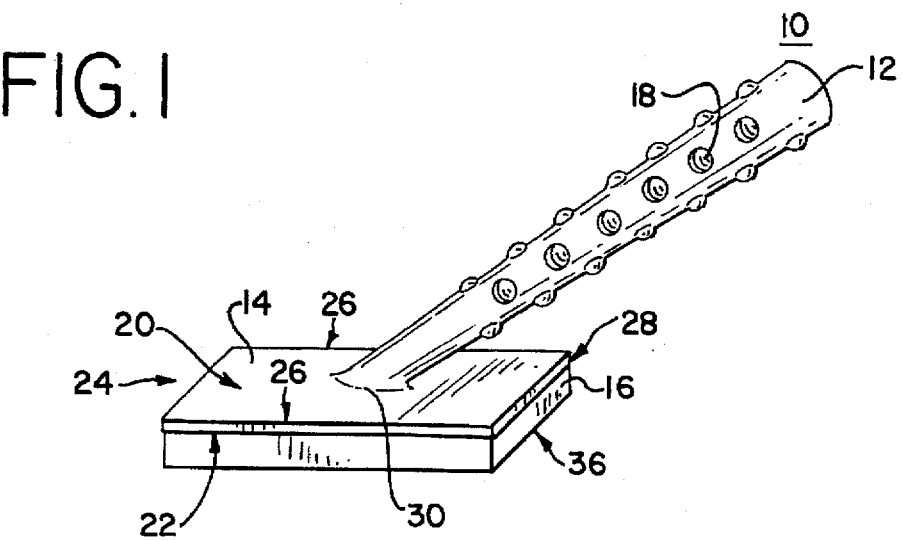
FIG. 1 is perspective view of one embodiment of the present invention.

Referring to FIG. 1, the bone wax applicator generally designated as 10, includes a handle 12 and a foot plate 14 to which the bone wax 16 is secured for application. The handle 12 is provided with grips 18 to reduce possible slippage during use. Grips 18 of other shapes can also be used. In FIG. 1, the handle 12 is depicted as a tapered and tubular structure, but such a shape is not critical, and other structures, such as a flattened oval cross-sectional handle, may be functionally equivalent or even better. However, it is important that no sharp edges are present. Sharp edges may compromise the integrity of surgical gloves which are usually worn by the user.

The foot plate 14 is generally planar, having an upper surface 20 and a lower surface 22. The foot plate 14 is generally defined by a front 24, two sides 26, and a back 28. The upper surface 20 has a center 30 near which the handle 12 is attached. During use of the applicator 10, the user usually presses the bone wax 16 onto the bone, exerting stress at the joint where the handle 12 is attached to the foot plate 14. By attaching the handle 12 near the center 30 of the foot plate 14, the stress at the joint is thereby reduced. Though FIG. 1 depicts a rectangular foot plate 14, a foot plate 14 of other shapes, such as a circle or an oval, may serve equally well.

Figure 2:
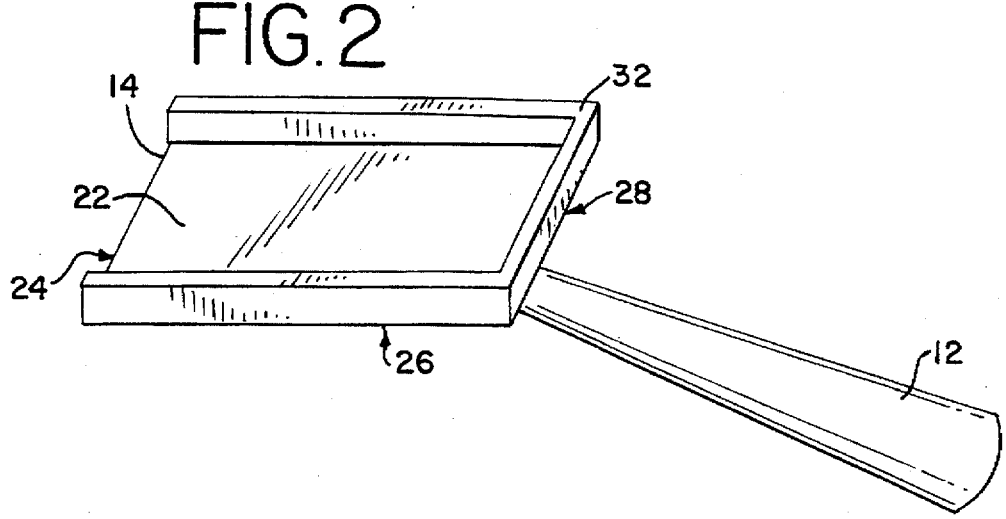
FIG. 2 is a perspective view of another embodiment of the present invention showing the lower surface of the foot plate.
Figure 3:
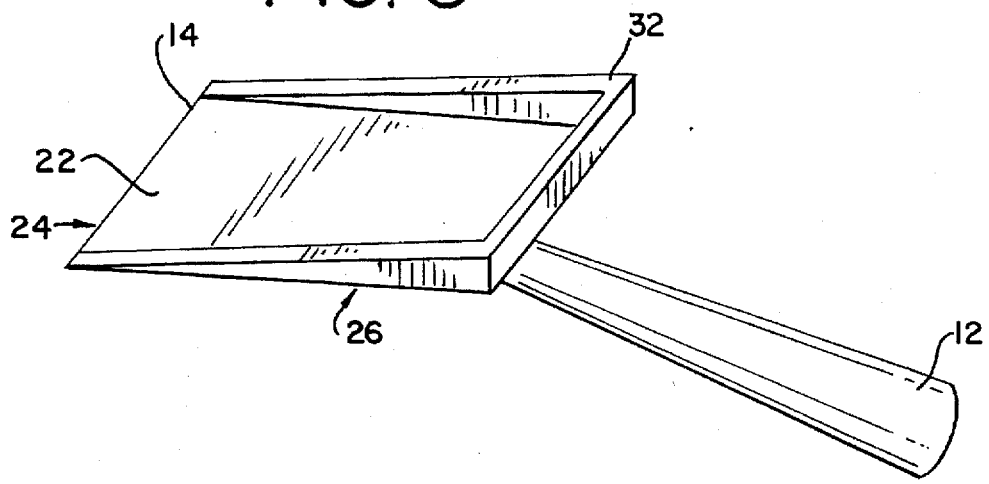
FIG. 3 is a perspective view of another embodiment of the present invention also showing the lower surface of the foot plate.

Turning now to FIG. 2, another embodiment of the present invention is depicted. In this embodiment, a raised edge 32 is provided along the two sides 26 and the back 28 of the foot plate 14. The raised edge 32 allows the foot plate 14 to better hold the bone wax 16 (not shown in FIG. 2) in place during use, and also allows the user to apply bone wax 16 from the foot plate 14 onto the bleeding bone tissue with forward thrusting motions. The front 24 of the foot plate 14 is not provided with a raised edge 32 so that it will not interfere with the use of the present applicator 10. The front 24 of the foot plate 14 can be used to accurately apply bone wax 16 onto a particular location. Further enhancing this feature, the raised edge 32 can be tapered to decrease toward the front 24 as depicted in FIG. 3.

With the present invention, bone wax 16 can be applied without obstructing the user's view since the handle 12 allows the user's hand to remain away from the bleeding area. Since the user's hand is away from the bleeding area, the possibility of the user's surgical glove being penetrated by the bone or other objects is also reduced. The handle 12 also allows the user to easily reach locations which would otherwise be difficult or impossible to reach.

Figure 4A:
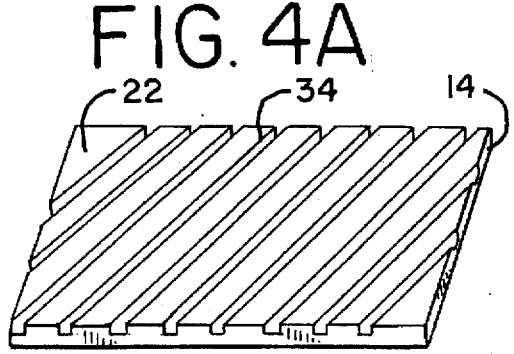
FIGS. 4A–4D are perspective views of the lower surface of the foot plate showing various patterns which can be provided on the foot plate.
Figure 4B:
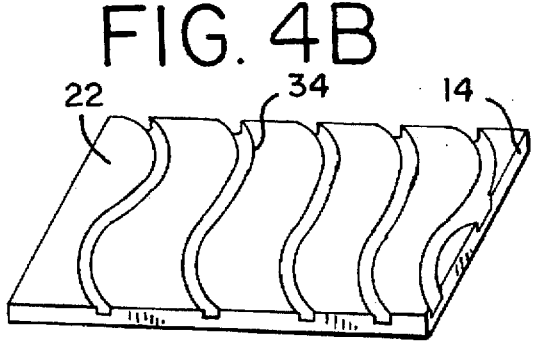
Figure 4C:
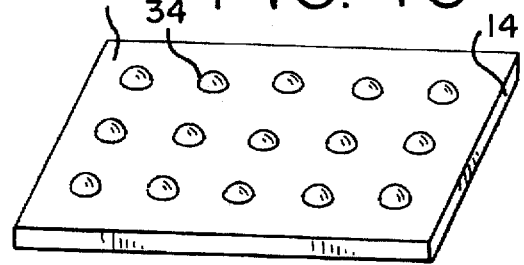
Figure 4D:
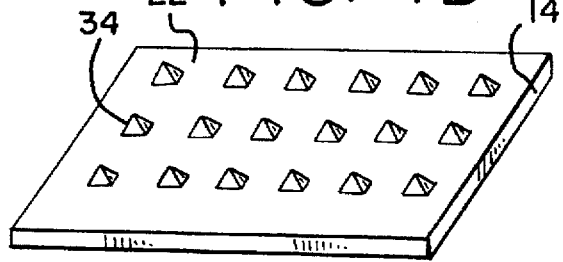
Figure 5A:
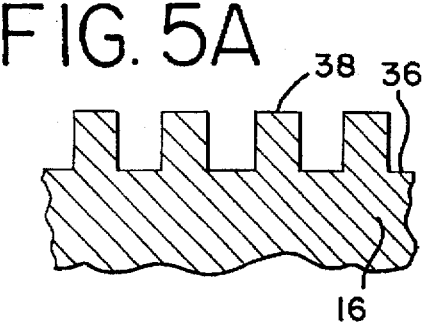
FIGS. 5A–5E are side sectional views of the free surface of the bone wax showing various patterns.
Figure 5B:
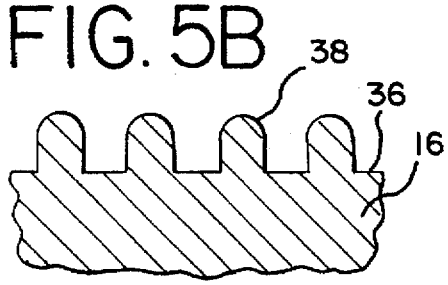
Figure 5C:
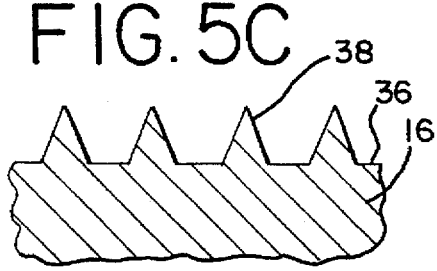
Figure 5D:
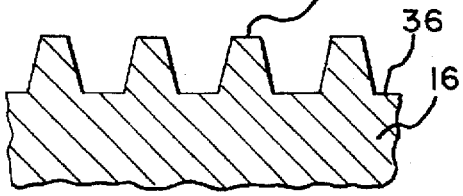
Figure 5E:
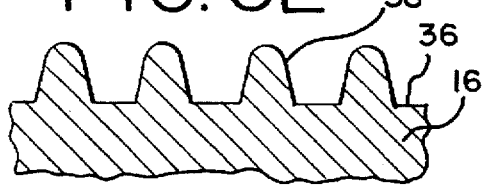

Referring now to FIGS. 4A–4D, the lower surface 22 of the foot plate 14 can be provided with patterns 34. The patterns 34 assist in holding the bone wax 16 (not shown in FIGS. 4A–4D) onto the lower surface 22 of the foot plate 14. The patterns 34 can be etched into the lower surface 22 as shown in FIGS. 4A and 4B, or the patterns 34 can be raised out of the lower surface 22 as shown in FIGS. 4C and 4D. The fact that the patterns 34 in 4A and 4B are etched into the lower surface 22 rather than raised is not significant. Any pattern 34 can be either raised or etched properly on the lower surface 22. FIGS. 4A–4D only show a sample of patterns 34 which can be used, and it is contemplated that many other patterns 34 can be used to achieve the same purpose.

Since the applicator 10 is generally used in surgical procedures, at least a portion of the applicator 10 should comprise or include material, in the resin forming the applicator, which is radio-opaque (detectable with an X-ray apparatus), such as barium sulfate. This feature will assist in locating the applicator 10 should it inadvertently be left behind in the patient's body after the operative site is closed. Additionally, it is preferable that the applicator 10 be disposable, i.e. single use, to further reduce the possibility of contamination.

Referring to FIG. 1, the bone wax 16 is positioned on the lower surface 22 of the foot plate 14. The lower, or free, surface 36 of the bone wax 16 can have no pattern or any number of patterns 38 as shown in FIGS. 5A–5E. The patterns 38 on the free surface 36 of the bone wax 16 increase the surface area with respect to volume, and thereby provide more bone wax 16 at the point of application. Furthermore, the patterns 38 will also provide the user with greater gripping power of the bone wax 16 as it is applied to the bleeding bone tissue.

While particular embodiments of the present invention have been shown and described, it will be appreciated by those skilled in the art that changes and modifications may be made thereto without departing from the invention in its broader aspects and as set forth in the following claims.

I claim:

1. A bone wax applicator system comprising, in combination:

bone wax; and an applicator, said applicator comprising a foot plate having an upper and a lower planar surface, the bone wax secured to said lower planar surface, said applicator further comprising a handle having a first and second end, said first end attached to said upper surface of said foot plate.

2. The bone wax applicator system as defined in claim 1 wherein said lower surface is defined by a perimeter, said lower surface provided with a raised edge along at least a portion of said perimeter for better holding and applying the bone wax.

3. The bone wax applicator system as defined in claim 1 wherein said foot plate is provided with a pattern on said lower surface, said pattern increasing the surface area of said lower surface and enhancing the ability of said lower surface to hold the bone wax.

4. The bone wax applicator system as defined in claim 1 wherein said upper surface has a center, said first end of said handle secured to said foot plate near said center of said upper surface.

5. The bone wax applicator system as defined in claim 1 wherein said handle is provided with a gripping surface to reduce possible slippage during use.

6. The bone wax applicator system as defined in claim 1 wherein at least a portion of said applicator includes radio-opaque material.

7. A bone wax applicator system comprising, in combination:

bone wax; and an applicator, said applicator comprising a foot plate having an upper and lower surface, said upper surface having a center, the bone wax attached to said lower surface, said lower surface provided with a pattern to better hold said bone wax, said applicator further comprising a handle having a first end and a second end, said first end connected near said center of said upper surface.

8. The bone wax applicator system as defined in claim 7 wherein said handle is provided with grips to reduce the possibility of slippage during use.

9. The bone wax applicator system as defined in claim 8 wherein at least a portion of said bone applicator comprises a radio-opaque material, whereby said applicator can be detected by an x-ray apparatus.

10. A surgical wax applicator system comprising, in combination:

bone wax having an attachment surface and a free surface; and an applicator, said applicator comprising a rectangular foot plate defined by a front, a back, and two sides, said foot plate further defined by an upper and lower surface, said upper surface having a center, said back and two sides having a raised edge depending down therefrom, said bone wax secured at said attachment surface to said lower surface of said foot plate, whereby said raised edge is provided for better holding said bone wax on said lower surface, said applicator further comprising a handle having a first and second end, said first end connected near said center of said upper surface.

11. The surgical wax applicator system as defined in claim 10 wherein said lower surface of said footplate is provided with a pattern, whereby said pattern enhances the ability of said lower surface to hold the wax.

12. The surgical wax applicator system as defined in claim 10 wherein said free surface of said bone wax is provided with a pattern, whereby said pattern increases the surface area of said bone wax and also enhances the gripping ability of said bone wax.

13. The surgical wax applicator system as defined in claim 10 wherein said handle is provided with grip structures to reduce the possibility of slippage during usage.

14. The surgical wax applicator system as defined in claim 10 wherein at least a portion of said applicator comprises a radio-opaque material.

15. The surgical wax applicator system as defined in claim 11 wherein at least a portion of said applicator comprises a radio-opaque material.

16. The surgical wax applicator system as defined in claim 11 wherein said free surface of said bone wax is also provided with a pattern, whereby said pattern increases the surface area of said bone wax and also enhances the gripping ability of said bone wax.

17. The surgical wax applicator system as defined in claim 16 wherein at least a portion of said applicator comprises a radio-opaque material.

* * * * *